United States Patent
Lindau et al.

(10) Patent No.: US 10,261,059 B1
(45) Date of Patent: Apr. 16, 2019

(54) GALVANIZATION ANALYSIS SYSTEM

(71) Applicant: Design Data Corporation, Lincoln, NE (US)

(72) Inventors: Brandon J. Lindau, Garland, NE (US); Michael T. Obst, Lincoln, NE (US)

(73) Assignee: DESIGN DATA CORPORATION, Lincoln, NE (US)

( * ) Notice: Subject to any disclaimer, the term of this patent is extended or adjusted under 35 U.S.C. 154(b) by 1198 days.

(21) Appl. No.: 13/861,545

(22) Filed: Apr. 12, 2013

Related U.S. Application Data

(60) Provisional application No. 61/624,213, filed on Apr. 13, 2012.

(51) Int. Cl.
*G01N 30/00* (2006.01)
*C23C 2/04* (2006.01)
*G01N 31/22* (2006.01)
*G01N 33/00* (2006.01)

(52) U.S. Cl.
CPC .............. *G01N 31/22* (2013.01); *G01N 33/00* (2013.01)

(58) Field of Classification Search
CPC .... G01N 30/00; G01N 2030/567; C23C 2/00; C23C 2/04; C23C 2/28; C23C 4/00; C23C 4/04
See application file for complete search history.

(56) References Cited

U.S. PATENT DOCUMENTS 6,140,825 A 10/2000 Fuji
6,583,386 B1 6/2003 Ivkovich

FOREIGN PATENT DOCUMENTS

WO WO2010/033113 A1 3/2010

OTHER PUBLICATIONS

Toi et al., Thermal Elasto-Viscoplastic Damage Behavior of Structural Members in Hot-Dip Galvanization, Apr. 2002, International Journal of Damage Mechanics, vol. 11, pp. 171-185.*

* cited by examiner

*Primary Examiner* — Toan Le
(74) *Attorney, Agent, or Firm* — Milligan PC LLO

(57) ABSTRACT

A computing device is described that is configured to analyze whether at least one structural member can be galvanized. In an implementation, the computing device includes a memory and a processor communicatively coupled to the memory. The computing device includes a module stored in memory and executable by the processor. The module is configured to instruct the processor to receive at least one structural member parameter. The structural member parameter is associated with a physical property of a structural member. The module is configured to analyze whether the structural member can be galvanized based upon the at least one structural member parameter.

1 Claim, 2 Drawing Sheets

GALVANIZATION ANALYSIS SYSTEM

CROSS-REFERENCE TO RELATED APPLICATIONS

The present application claims the benefit under 35 U.S.C. § 119(e) of U.S. Provisional Application Ser. No. 61/624,213, entitled GALVANIZATION ANALYSIS SYSTEM, filed on Apr. 13, 2012. U.S. Provisional Application Ser. No. 61/624,213 is herein incorporated by reference in its entirety.

BACKGROUND

Galvanization, such as hot-dip galvanization, is the process of applying a protective zinc coating to steel or iron members to prevent rusting. These members are typically degreased, or cleaned, first with an alkali solution that removes organic contaminants (e.g., dirt, paint, grease, etc.). After degreasing, the member is rinsed with water. The member is then moved to a pickle bath, which is an acidic solution, that removes iron oxides from the surface of the member. The member is then moved into a pre-flux tank to remove any remaining iron oxides, as well as provide a protective layer to at least substantially prevent any iron oxide formation prior to immersing the member in a galvanizing kettle. The member is then completely immersed in a zinc bath.

SUMMARY

A computing device is described that is configured to analyze whether at least one structural member (e.g., a steel structural member) can be galvanized. In an implementation, the computing device includes a memory and a processor communicatively coupled to the memory. The computing device includes a module stored in memory and executable by the processor. The module is configured to instruct the processor to receive at least one structural member parameter. The structural member parameter is associated with a physical property of a structural member. The module is configured to analyze whether the structural member can be galvanized based upon the at least one structural member parameter.

This Summary is provided solely to introduce subject matter that is fully described in the Detailed Description and Drawings. Accordingly, the Summary should not be considered to describe essential features nor be used to determine scope of the claims.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different instances in the description and the figures may indicate similar or identical items.

DETAILED DESCRIPTION

Figure 1:
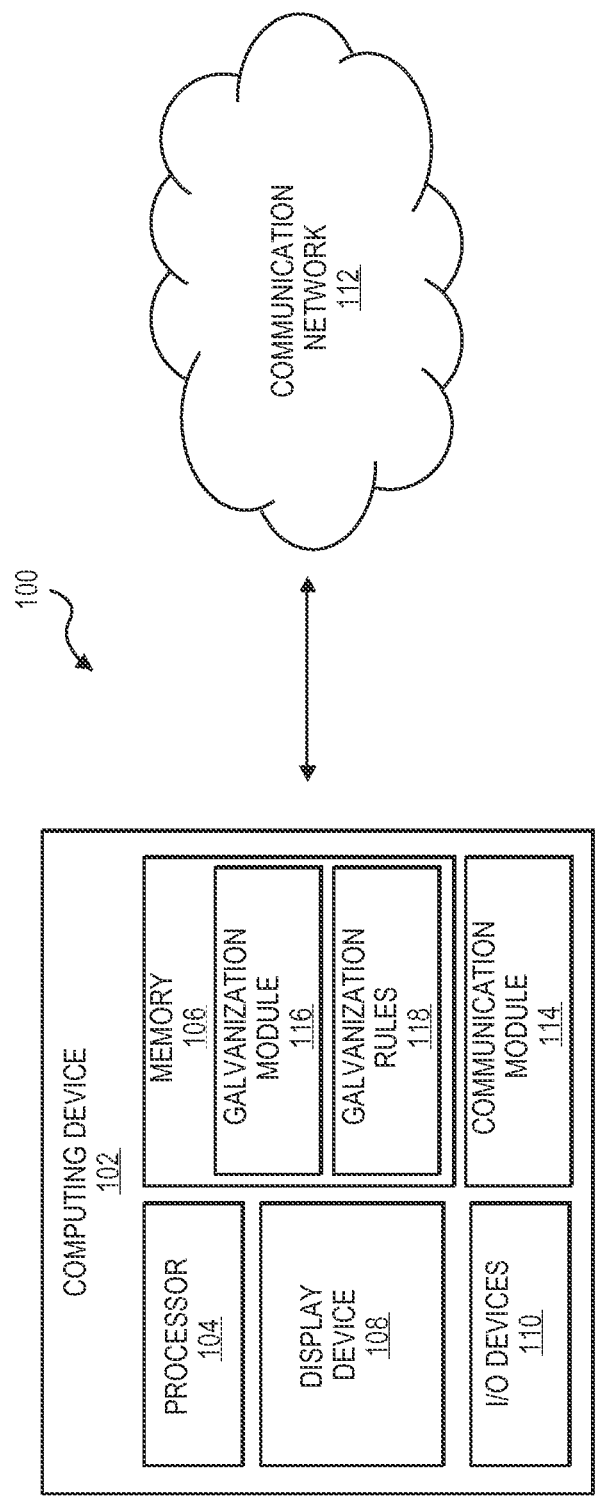
FIG. 1 is a block diagram of a system in accordance with example implementations of the present disclosure.

FIG. 1 illustrates a system 100 for analyzing, or determining, whether a member (e.g., a steel structural member, etc.) can be analyzed based upon one or more parameters that define physical properties/characteristics of the member. For example, the set of parameters is utilized by the system 100 to determine whether, based upon the defined properties, the corresponding physical member (e.g., the physical structural steel members utilized to construct buildings, etc.) can be galvanized via a hot dip galvanizing process. For instance, a user can define such parameters as the material type of the member, dimensions of the member, vent/drain holes defined by the material of the member, and so forth, within the system 100, and the system 100 is configured to analyze whether the corresponding physical member can be galvanized. It is contemplated that the user may be a detailer tasked with producing detailed drawings for steel fabricators and steel erectors. It is also contemplated that the user may be a fabricator tasked with building the members (e.g., structural members) by cutting, bending, and assembling. As shown, the system 100 includes a computing device 102. In one or more implementations, the computing device 102 may be a server, a desktop computing device, a laptop computing device, or the like. As shown in FIG. 1, the computing device 102 includes a processor 104 and a memory 106.

The processor 104 provides processing functionality for the computing device 102 and may include any number of processors, micro-controllers, or other processing systems and resident or external memory for storing data and other information accessed or generated by the computing device 102. The processor 104 may execute one or more software programs (e.g., modules) that implement techniques described herein.

The memory 106 is an example of tangible computer-readable media that provides storage functionality to store various data associated with the operation of the computing device 102, such as the software program and code segments mentioned above, or other data to instruct the processor 104 and other elements of the computing device 102 to perform the steps described herein.

The computing device 102 is also communicatively coupled to a display device 108 to display information to a user of the computing device 102. In embodiments, the display device 108 may comprise an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. For example, the display 108 displays visual output to the user. The visual output may include graphics, text, icons, video, interactive fields configured to receive input from a user, and any combination thereof (collectively termed "graphics").

As shown in FIG. 1, the computing device 102 is also communicatively coupled to one or more input/output (I/O) devices 110 (e.g., a keyboard, buttons, a wireless input device, a thumbwheel input device, a trackstick input device, a touchscreen, and so on). The I/O devices 110 may also include one or more audio I/O devices, such as a microphone, speakers, and so on.

The computing device 102 is configured to communicate with one or more other computing devices over a communication network 112 through a communication module 114. The communication module 114 may be representative of a variety of communication components and functionality, including, but not limited to: one or more antennas; a browser; a transmitter and/or receiver (e.g., radio frequency circuitry); a wireless radio; data ports; software interfaces and drivers; networking interfaces; data processing components; and so forth.

The communication network 112 may comprise a variety of different types of networks and connections that are contemplated, including, but not limited to: the Internet; an intranet; a satellite network; a cellular network; a mobile data network; wired and/or wireless connections; and so forth.

Wireless networks may comprise any of a plurality of communications standards, protocols and technologies, including, but not limited to: Global System for Mobile Communications (GSM), Enhanced Data GSM Environment (EDGE), high-speed downlink packet access (HS-DPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS), and/or Short Message Service (SMS)), or any other suitable communication protocol.

Figure 2:
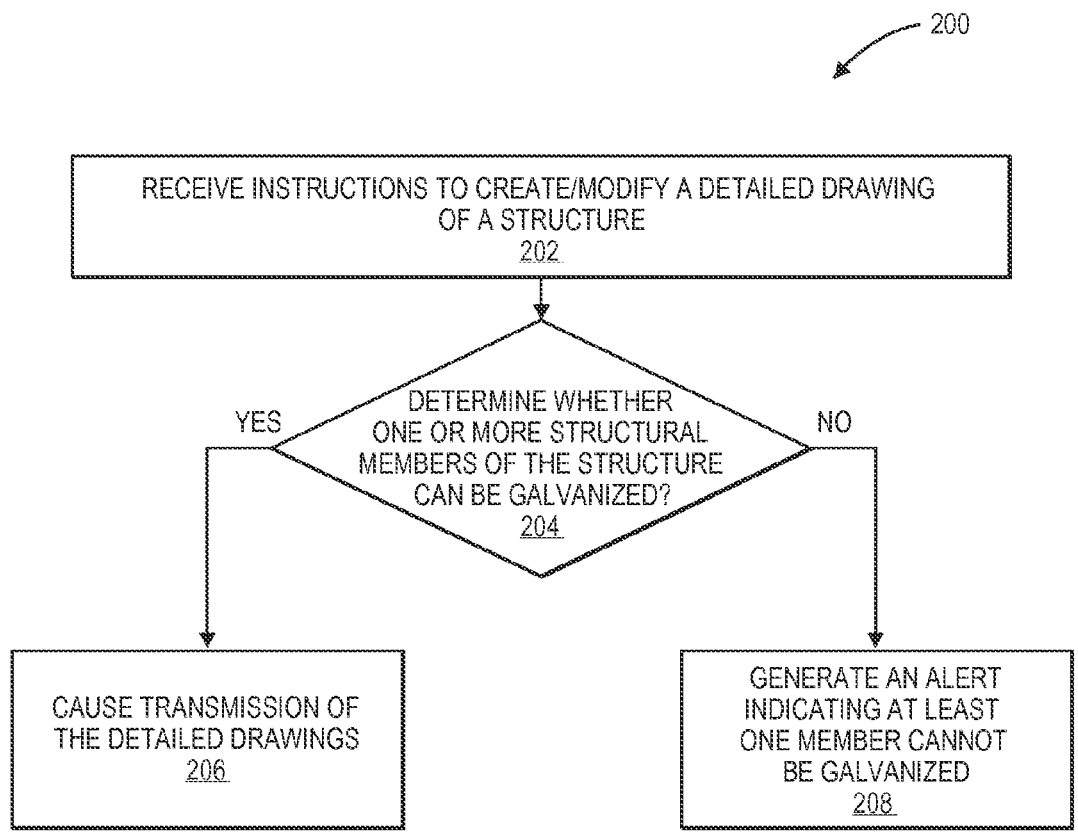
FIG. 2 is a flow diagram illustrating an example process in accordance with the present disclosure.

Galvanization, such as hot-dip galvanization, is a process of applying a protective zinc coating to steel or iron members to prevent rusting. These members are typically degreased with an alkali solution that removes organic contaminants. After degreasing, the member is rinsed with water. The member is then moved to a pickle bath, which is an acidic solution, that removes iron oxides from the surface of the member. The member is then moved into a pre-flux tank to remove any remaining iron oxides to at least substantially prevent any iron oxide formation prior to immersing the member in a galvanized kettle. The member is then completely immersed in a zinc bath. FIG. 2 illustrates a process 200 for determining whether a member can be galvanized. The user may utilize a structural modeling software package to create detailed drawings for a structure. For example, the processor 104 may receive instructions to create/modify detailed drawings for the structure (Block 202). For example, the user may generate computer-generated drawings and plans representing/modeling a structure to be built. These drawings/plans may include information that conveys the desired placement of one or more structural members (columns, beams, connectors, fasteners, and so forth) that comprise the structure to be built. In an implementation, the drawings may be conveyed in an orthographic (three-dimensional) environment. Additionally, the drawings/plan may include parameters that define physical properties of the structural members. Based upon the placement of one or more structural members, the user may wish to indicate that the structural members should be galvanized due to exposure to a corrosive environment. Thus, the user may utilize the system 100 to analyze whether the members can be galvanized based upon the parameters provided in the drawings/plans, which is described in greater detail below.

The computing device 102 includes a galvanization module 116, which is storable in memory 106 and executable by the processor 104. The galvanization module 116 is representative of functionality to analyze (determine) whether members (e.g., steel structural members, etc.) selected to be galvanized are within an acceptable galvanization criteria (e.g., low risk of air pockets, etc.). As shown in FIG. 2, a determination is made of whether one or more structural members can be galvanized (Decision Block 204). For instance, the detailed drawings may include parameters representing various physical characteristics of the structural parameters. For example, the members may be structural members (e.g., columns, beams, trusses, braces, etc.). The acceptable galvanization criteria are defined by a set of galvanization rules and/or standards 118. In an implementation, the galvanization rules 118 are set forth by one or more governing bodies specializing in galvanizing members, such as structural steel members. For example, the rules 118 may be set forth by the American Galvanizers Association (AGA), or a similar galvanizer governing body. Thus, the rules 118 are utilized by the module 116 to cause the processor 104 to determine whether a member can be galvanized based upon one or more member parameters and/or galvanizing parameters. Thus, the system 100 functions as a rule based galvanization check system. The module 116 may also be configured to cause the processor 104 to generate a galvanizing report for each member analyzed.

As described above, the processor 104 can determine whether a member can be galvanized based upon one or more member and galvanizing parameters. For example, the member parameters may include structural member design parameters, and the galvanizing parameters may include parameters associated with the galvanizing process. The member parameters may be structural related design parameters including, but not limited to: member material type, a number of vent and/or drain holes defined within the member, size of the member (e.g., length, width, depth, diameter, thickness), a plate type of the member, a bolt diameter to be utilized within the member, grade of steel, type of holes defined by the member material, whether the member is coupled to another member, conflicting material thickness, welding types (e.g., proper use of seal/stagger welds), use of galvanized fasteners, and so forth. The galvanizing parameters may include, but are not limited to: size of the galvanizing kettle (e.g., length, width, depth of the kettle), size of the preparation baths, a kettle crane capacity, and so forth. The user may select/unselect one or more galvanization rules to be applied during the analysis of the selected steel members.

Initially, the module 116 is configured to cause a processor 104 to initiate display of one or more interactive graphics (e.g., text input fields, drop down menus, check boxes, etc) at the display device 108 to allow the user to define parameters associated with each member to be galvanized. In an implementation, a user may utilize the I/O devices 110 to input one or more user-provided parameters to define various member parameters and/or galvanizing parameters. For example, the user can define parameters of the galvanizing kettle (e.g., length, width, depth), a member surface finish (e.g., galvanized, duplex coating), hole types (e.g., vent/drain, bolt, etc.), hole diameters, type of plugged hole (e.g., zinc plugged, welded, etc.), types of fasteners utilized to fasten multiple members together, flange member type (e.g., wide flange beam, etc.), and so forth. In another example, one or more of the parameters may include default settings (e.g., default kettle dimension settings, member surface finish, etc.).

In some implementations, multiple members may comprise a single structural entity in a detailed structural drawing, or the like (e.g., a beam coupled to a column with four (4) connectors). In this implementation, the user may provide input to signify to the module 116 that each member of the single entity must be analyzed separately. For example, an interactive detailed structural drawing representing the single structural entity is displayed via the display device 108. The user can select the single structural entity (e.g., mouse over and click, etc) that causes the processor 104 to initiate display of an interactive graphic that allows the user to select one or more galvanizing parameter options. One of the options includes the ability to cause the module 116 to instruct the processor 104 to analyze each member separately (e.g., beam is analyzed to determine whether the beam can be galvanized, each connector is analyzed separately to determine whether the respective connector can be galvanized).

As described above, the module 116 is configured to cause the processor 104 to determine whether one or more members can be galvanized based upon the member parameters. Thus, once the user provides the required parameters (or does not modify the default parameters), the module 116 is configured to analyze the selected members. For example, the user may provide, or modify, one or more parameters defining properties of one or more structural steel members. The module 116 is configured to cause the processor 104 to analyze the parameters and/or the properties of the members to determine whether the members can be galvanized based upon the parameters and/or properties furnished. In an implementation, the module 116 is configured to cause the processor to cross-reference the furnished parameters/properties with the galvanization rules 118. For example, each parameter defining the physical characteristics (e.g., dimensions of the member, number and location of vent/drain holes, etc.) of the member is cross-referenced with the corresponding value within the rules 118.

If each property falls within an acceptable range as defined by the rules 118, the processor 104 determines the member can be galvanized (e.g., falls within the acceptable galvanization criteria). If one or more parameters fall outside the acceptable range defined by the rules 118, the processor 104 determines the member cannot be galvanized. For instance, based upon the cross-referencing of the parameters with the rules 118, a structural member may be sealed, which may indicate the presence of air pockets. In another instance, a type of welding between members may be deemed unacceptable due to an increased risk of corrosion. The module 116 is configured to cause the processor to initiate display of one or more rules 118 that were deemed outside the acceptable range. Thus, the user may be required to modify one or more parameters (e.g., properties) of the members, or modify structural members (e.g., break a single structural entity into multiple structural entities) as a whole, to allow for galvanization of the desired members. For example, the user may be required to modify the design of one or more structural members, include additional vent/drain holes, or the like. In another example, the user may be required to break down the structural member into smaller, independent pieces to be re-assembled after the galvanization process (e.g., dimensions of the structural member do allow the physical member to fit in the preparation tanks and/or the galvanization kettle).

If the members can be galvanized (YES from Decision Block 204), the detailed drawings are transmitted (Block 206) to initiate fabrication of the structural members. For example, the module 116 is configured to cause the processor 104 to transmit the drawings/plans to other remote computing devices (e.g., remote devices of members) associated with the design/fabrication of the structure (e.g., steel fabricators, galvanizers, etc.) to initiate fabrication of the structural members. If the members are not in a condition to be galvanized (NO from Decision Block 204), an alert is generated to convey that the members are not in a condition to be galvanized (Block 208). For example, the module 116 is configured to cause the processor 104 to initiate an alert that conveys this information to the user. For example, the module 116 may cause the processor 104 to initiate display of information conveying which members are not suitable to be galvanized and the parameters that cause the member(s) to fail the galvanize check. As described above, the user may be required to modify one or more parameters of the member, modify at least a portion of the structure to be build (e.g., utilize other members), and so forth.

Additionally, the module 116 is configured to cause the processor 104 to generate a report. The report may include a summary of galvanized members, material, vent/drain plug hole type, and so forth, which may be utilized by the galvanizer, or the like. This report may also be transmitted to one or more members associated with the fabrication of the structure. Additionally, the module 116 may be configured as a stand-alone application, or be integrated with a structural modeling software package, such as SDS/2 software package developed by Design Data.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method of selecting and galvanizing a metal member to apply a protective zinc coating to the metal member, wherein the method comprises:

inputting orthographic data representing a three-dimensional steel structure; wherein steel structure is comprised of one or more structural entities; wherein the one or more structural entities are comprised of at least two or more steel members; wherein the steel members are comprised of at least one steel member selected from the group of steel member which comprises: columns, beams, trusses, braces, rivets and nuts;

inputting and storing galvanizing parameters for a selected galvanizing process; wherein galvanizing parameters are selected from the group of parameters comprising: the size of a galvanizing kettle, size of a preparation bath and the capacity of a kettle crane, surface finish, hole types, hole diameters, type of plugged hole, types of fasteners utilized to fasten multiple members together and flange type;

selecting a first structural entity to be galvanized;

identifying the steel members of the first structural entity;

extracting a first structural parameter for the first structural entity as a whole; wherein the first structural parameter of the first structural entity as a whole is comprised of one or more dimensions of the first structural entity as a whole extracting a second structural parameter for each identified steel member of the first structural entity; wherein the second structural parameter is comprised of a material type for each identified steel member;

extracting a third structural parameter for each identified steel member of the first structural entity; wherein the third structural parameter is comprised of one or more dimensions of each identified steel member;

extracting a fourth structural parameter for each identified steel member of the first structural entity, wherein the fourth structural parameter is comprised of a parameter selected from the group of parameters comprising: a plate type, a bolt diameter to be utilized within the member, grade of steel, type of holes defined by the steel member material, conflicting material thickness, welding types, and the use of galvanized fasteners;

comparing the extracted structural parameters from the steel members of the first structural entity to one or more of the stored galvanizing parameters;

determining whether the extracted structural parameters for the first structural entity as a whole are within an acceptable range for a stored galvanizing parameter;

determining whether the extracted structural parameters for each steel member of the first structural entity are within an acceptable range for each stored galvanizing parameter;

identifying a new structural configuration for the first structural entity having new structural parameters, wherein the new structural configuration is created by excluding a steel member which is not within an acceptable range for a stored galvanizing parameter;

identifying a new structural configuration for the first structural entity having new structural parameters, wherein the new structural configuration is created by excluding a steel member; wherein excluding the steel member changes the structural parameters of a first structural entity as a whole to be within an acceptable range for a stored galvanizing parameter;

selecting a first group of steel members forming the new structural configuration; wherein the first group of steel members comprise steel members which are not excluded from the new structural configuration;

identifying a first selected steel member from the first group of selected steel members for galvanization;

generating an alert conveying that at least one structural member cannot be galvanized when the at least one structural member cannot be galvanized;

applying an alkali solution to the first steel member;

rinsing the first steel member in a water solution;

applying an acid solution to the first steel member;

placing the first steel member in a pre-flux tank to remove any remaining iron oxides on the first steel member; and immersing the first steel member in zinc solution.

* * * * *